United States Patent [19]

Murray et al.

[11] Patent Number: 4,724,145

[45] Date of Patent: Feb. 9, 1988

[54] *EIMERIA ACERVULINA* IMMUNOGENS

[75] Inventors: Peter K. Murray, Red Bank; Balbir S. Bhogal, Avenel, both of N.J.; Ethel B. Jacobson, New York, N.Y.; Mark S. Crane, Westfield, N.J.; Dennis M. Schmatz, Cranford, N.J.; Stefan Galuska, North Plainfield, N.J.

[73] Assignee: Merck & Co., Inc., Rahway, N.J.

[21] Appl. No.: 798,775

[22] Filed: Nov. 18, 1985

[51] Int. Cl.$^4$ ................. A61K 39/012; A61K 39/002
[52] U.S. Cl. ........................................ 424/88; 424/93; 530/350; 530/822; 435/68; 435/243; 435/258; 435/803; 435/947
[58] Field of Search ................... 530/350, 822; 424/88, 424/93; 435/68, 803, 947, 243, 258

[56] References Cited

U.S. PATENT DOCUMENTS

| | | | |
|---|---|---|---|
| 4,438,097 | 5/1984 | Shirley | 424/88 |
| 4,639,372 | 1/1987 | Murray et al. | 424/88 |
| 4,650,676 | 3/1987 | Schenkel et al. | 424/88 |

FOREIGN PATENT DOCUMENTS

| | | |
|---|---|---|
| 0135073 | 8/1983 | European Pat. Off. |
| 0135712 | 7/1984 | European Pat. Off. |
| 0167443 | 6/1985 | European Pat. Off. |
| 0164176 | 12/1985 | European Pat. Off. |

OTHER PUBLICATIONS

Danforth et al., Poultry Science 62, 1983, pp. 2145-2151.
Speer et al., Z Protozool 30(3) 1983, pp. 548-554.
Schmatz et al., J. Protozool 31(1) 1984, pp. 181-183.
Edgar, Trans. Am. Micro. Soc. 62: 237-242 (1954).
Erickson et al., J. Imm. Meths. 51: 241-249 (1982).
Johnson & Reid, Exp. Parasit. 28: 30-36 (1970).
Laemmli, Nature 227: 680-685 (1970).
Long & Rose, World's Poultry Sci. J. 38: 85-96 (1982).
Long & Rose, Exp. Parasitology 16: 1-7 (1965).
Lowry et al., J. Biol. Chem. 193: 265-275 (1951).
Patton, Science 150: 767-769 (1965).
Rose, In Biology of the Coccidia, P. L. Long, ed., University Park Press, Baltimore, pp. 329-371 (1982).
Rose & Hesketh, Parasitology 73: 25-37 (1976).
Schmatz et al., Protozool. 31: 181-183 (1984).
Towbin et al., Proc. Natl. Acad. Sci. USA 76: 4350-4354 (1979).

*Primary Examiner*—John Kight
*Assistant Examiner*—Garnette D. Draper
*Attorney, Agent, or Firm*—Jack L. Tribble; Donald J. Perrella; Hesna J. Pfeiffer

[57] ABSTRACT

High levels of immunity are achieved in chickens inoculated intramuscularly or orally with *E. acervulina* extract immunogens. These extracts contain at least 20 polypeptides which induce a protective immune response not only against *E. acervulina* but also against *E. tenella* and *E. maxima*. The resulting immunity prevents intestinal lesions and reduces the number of viable oocysts in vaccinated and challenged birds. One or more of these polypeptides can be used as an immunogen to protect against coccidiosis.

9 Claims, No Drawings

EIMERIA ACERVULINA IMMUNOGENS

BACKGROUND OF THE INVENTION

Coccidiosis is a disease caused by infection with one or more of the many species of coccidia, a subdivision of the phylum Protozoa. The coccidia are intracellular parasites which can infect a wide range of hosts and may result in severe economic loss to the sheep, goat, cattle, swine and poultry industry. Indeed, coccidiosis resulting from infection with Eimeria species has caused economically devastating losses to the poultry industry. Among domesticated birds, chickens are the most susceptible to the economic losses from coccidiosis, although losses can also occur with turkeys, geese, ducks, and guinea fowl. Coccidiosis also produces serious losses in pheasants and quail raised in captivity. Coccidiosis may be acute and characterized by devastating flock mortality or the disease may be chronic and characterized by a lack of weight gain.

Poultry are infected by coccidia following ingestion of the vegetative stage of the parasite, the sporulated oocyst. The infective stage, the sporozoite, is released in the intestine where it rapidly invades epithelial cells subsequently undergoing several generations of rapid intracellular asexual multiplication before entering the stage of sexual differentiation leading to the production of oocysts which are shed in the droppings. Low level infection with any of the Eimeria species (spp.) results in a protective immunity to reinfection. This has suggested that coccidiosis may be controlled by the use of live vaccines. The development of effective vaccines has been slowed by the complex life cycle of Eimeria and the fact that post infection immunity is generally species specific (Long and Rose, Worlds Poultry Sci. J. 38: 85–96, 1982). It has been shown that the infection must progress as far as the development of asexual stages before immunity is induced. Thus, the immunizing antigens for at least some species are likely to be contained in the asexual stages (Rose and Hesketh, Parasitology 73: 25–37, 1976). However, the sporozoite stage appears to have little immunizing value (Rose, M. E., 1982, Biology of the Coccidia, P. L. Long, ed., University Park Press, Baltimore, p. 329, 1982).

Previous attempts to immunize chickens with non-viable Eimeria components have been unsuccessful. Parenterally administered soluble Eimeria antigens failed to reduce subsequent challenge with infective sporozoites (Long and Rose, Exp. Parasitology 16: 1–7, 1965). Conversely, solubilized E. tenella sporozoite antigens have been used to protect chickens against challenge with E. tenella, Schenkel et al., European Patent Application No. 0135712, while solubilized merozoite antigens have been regarded as a potential vaccine, Schenkel et al., European Patent Application No. 0135073.

SUMMARY OF THE INVENTION

Extracts are prepared by grinding sporulated oocyst of E. acervulina followed by freeze-thawing and sonication of the supernatant liquid. The sporozoite extract is prepared by freeze-thawing and sonication of DE-52 anion exchange purified sporozoites. The sporozoite extracts contain polypeptides which induce specific antibody responses. Of these polypeptides, 20 are immuno dominant i.e., the 20, 21.5, 22.5, 23, 24, 26, 26.5, 27, 29, 31, 34, 37, 41.5, 45, 59, 65, 68, 74, 84 and 115 kd molecular weight polypeptides. Sera containing antibody reactive with these polypeptides neutralize sporozoite infectivity in unimmunized challenged chickens. One or more of these polypeptides can be used as an immunogen to prophylactically immunize against the morbidity and mortality caused by virulent infection with E. acervulina, E. tenella or E. maxima.

OBJECTS OF THE INVENTION

It is, accordingly, an object of the present invention to provide an extract of E. acervulina which contains immunogens that will induce protective immunity against coccidiosis. Another object is to provide immunogenic polypeptides of the type normally located on the surface or within intact oocysts or sporozoites. Another object is to provide a means for obtaining these immunogenic extracts. Another object is to provide compositions for the prophylactic administration of these immunogens. A further object is to provide a coccidiosis vaccine which is protective against those forms of Eimeria mainly responsible for economic loss. These and other objects of the present invention will be apparent from the following description.

DETAILED DESCRIPTION OF THE INVENTION

The present invention relates to a coccidiosis vaccine based on parasite extracts and one or more immunogenic polypeptides normally found on the surface of intact sporozoites and in sporulated occysts. The invention further relates to the immunogenic polypeptides themselves and to the methods of obtaining the extracts or immunogenic polypeptides and to their use in preparing a vaccine effective against coccidiosis.

Parasite extracts containing immunogenic polypeptides are obtained from (1) sporulated oocysts and/or, (2) sporozoites. Oocysts are isolated by physical disruption of fecal material from chickens about 6 days after infection. A fecal homogenate is filtered through cheese cloth and the debris is removed by washing and centrifugation. A partially pure oocyst fraction is collected by flotation on a solution of about 20% saline and rendered bacteria-free, e.g. by treatment with a hypochlorite solution, preferably sodium hypochloride, at a concentration of about 5 to about 6 percent in water at about 4° C. for approximately 10 minutes. The hypochlorite is removed by several washes with sterile buffered saline. Oocysts are allowed to sporulate following the technique of Edgar, Trans. Am. Micr. Soc., 62: 237–242, (1954).

Sporulated oocysts are suspended in a physiologically acceptable medium and disrupted according to the method of Patton, Science 150: 767–769 (1965). Such physiologically acceptable media include, but are not limited to, physiological saline, phosphate buffered saline, phosphate buffered saline glucose, buffered saline and the like. Sporocysts from the disrupted oocysts are separated by centrifugation at about 1000×g for approximately 10 minutes. The supernatant fluid is designated the post-grind supernatant (PGS) immunogen composite and the pelleted material containing sporocysts is further processed for sporozoites. The pelleted material is treated with an excysting solution containing about 0.125% trypsin and about 1.0% taurodeoxycholic acid in a buffer solution at between about 25° and about 41° C. in an atmosphere of about 5% $CO_2$–95% air for about one half hour. The excysting solution is removed by washing with a buffer solution and centrifugation.

The final pellet is resuspended in a physiologically acceptable media, as described above, and the sporozoites are isolated using a DE-52 anion exchange column employing the method of Schmatz et al. J. Protozool. 31: 181–183, (1984). The isolated sporozoites are thrice frozen and thawed in a buffer containing about 1 mM phenylmethylsulfonylfluoride and then sonically disrupted.

The polypeptides obtained from sporozoites are analyzed by linear gradient sodium dodecyl sulfate (SDS) polyacrylamide gel electrophoresis, with gels ranging from about 5 to about 20 percent polyacrylamide, under reducing conditions. Coomassie blue staining and comparison with molecular weight markers reveals 31 polypeptides ranging in size from about 300 kilodaltons (kd) to about 13 kd. When these polypeptides are admixed with rabbit anti-*E. acervulina* antibody utilizing a Western Blot analysis only 20 polypeptides show strong antibody binding. These immunodominant polypeptides of about 115, 84, 74, 68, 65, 59, 45, 41.5, 37, 34, 31, 29, 27, 26.5, 26, 24, 23, 22.5, 21.5 and 20 kd are capable either singly or in combination of inducing immune responses in chickens which protect them against coccidiosis induced by not only *E. acervulina* but other Eimeria species.

Chickens are immunized by inoculating the PGS immunogen composite or polypeptide immunogens listed above either singly or in combination or as a parasite extract in a physiologically acceptable medium. Immunization by the oral or intramuscular route in newly hatched or adult birds results in immunity to infection such that after exposure to the virulent parasite no significant disease results. Protective immunity is achieved by administration of from about 1 $\mu$g to about 200 $\mu$g, preferably from about 5 to about 75 $\mu$g, in a single dose or several divided doses, of polypeptide immunogen or immunogen composite per chicken on from about 1 to about 4 separate weekly occasions. The preferred dosage for two day old chickens immunized by either the intramuscular route or the oral route is about 1 $\mu$g given on day 2, 9 and 16 following hatching or a single dose of about 50 $\mu$g given on day 2 following hatching. Immunization of chickens with *E. acervulina* as described results not only in a significant protection to *E. acervulina* but unexpectedly there is also a significant immune protection to challenge with *E. tenella* or *E. maxima*.

The following examples illustrate the present invention without, however, limiting the same thereto.

EXAMPLE 1

Preparation of *E. acervulina* Oocysts and Oocyst Immunogens

Oocysts—*Eimeria acervulina* oocysts were obtained from adult chickens infected 5 to 6 days earlier with a stock cultures of *E. acervulina*. Feces and the intestinal contents from infected birds were collected, diluted with distilled water and disrupted in a Waring Blender. The disrupted material was filtered through cheese cloth. The particulate portion was washed with distilled water and collected by low speed centrifugation, 1000 $\times$ g. A partially pure oocyst fraction was isolated by flotation of the oocysts on a 20% saline solution and treated with 5.25% sodium hypochlorite at 4° C. for 10 minutes. The sodium hypochlorite was removed by several washes in sterile phosphate-buffered saline (PBS), pH 7.6, to obtain purified bacteria free oocysts.

Sporulated Oocysts—Oocysts prepared as above were sporulated in a shaking water bath at 29° C. for 48 hours. Sporulated oocysts were stored in PBS (pH 7.6) at 4° C. until use.

Post-grind Supernatant—A 2 ml suspension of purified sporulated oocysts ($5 \times 10^7$/ml PBS, pH 7.6) was ground at 700 rpm for 6 minutes at 4° C. in a tissue homogenizer with a loose-fitting pestile and the supernatant material was collected by centrifugation (1000 $\times$ g for 10 minutes). This milky, lipid-rich composite was designated post-grind supernatant (PGS) composite immunogen. The pelleted material was further processed for sporozoites as described in Example 2.

Prior to injection of the PGS into chickens it was freeze-thawed three times by rapid cooling to dry ice temperature followed by rapid warming to room temperature, and subsequently the PGS was sonicated in phosphate buffered saline containing 1 mM phenylmethylsulfonylfluoride to inhibit protein degradation.

EXAMPLE 2

Preparation of Sporozoite Immunogens

Sporozoites—The pelleted material obtained in Example 1, composed of unbroken oocysts, sporocysts and oocyst shells, was resuspended in an excysting solution containing 0.125% (w/v) trypsin (1:250) and 1.0% (w/v) taurodeoxycholic acid in Hank's balanced salt solution (pH 7.4) and incubated at 41° C. in 5% $CO_2$. After $\frac{1}{2}$ hour, the excysting solution was removed by centrifugation and parasite material was washed twice in phosphate buffered saline glucose (PBSG: 9.44 g/L anhydrous $Na_2HPO_4$, 0.55 g/L $NaH_2PO_4 2H_2O$, 2.98 g/L NaCl, 10 g/L glucose, pH 8.0). The parasite mixture was applied to a DE-52 anion exchange column equilibrated with PBSG. The sporozoites were purified from other parasite materials by elution in the void volume.

Sporozoite immunogens were obtained from sporozoites that were freeze thawed 3 times by cooling with dry ice and warming to room temperature, and sonicated until disrupted in PBS with 1 mM phenylmethylsulfonylfluoride as a protease inhibitor. Protein concentrations were determined by method of Lowry et al. (1951), J. Biol. Chem. 193: 265–275, and the immunogens were stored in liquid $N_2$.

EXAMPLE 3

Separation and Characterization of *E. acervulina* Sporozoite Polypeptide Immunogens Sporozoite immunogens obtained as described in Example 2 were separated into individual polypeptides according to size by sodium dodecyl sulfate (SDS) polyacrylamide gel electrophoresis (PAGE). Two hundred $\mu$g of sporozoite immunogen were separated on a 5–20% linear polyacrylamide gradient overlaid with a 3% polyacrylamide stacking gel in the presence of 0.1% SDS and 2-mercaptoethanol, Laemmli, Nature, 227: 680–685, (1970). The polypeptides were electrophoresed at 50 ma for 3–4 hours at 10–12° C. until the tracking dye, bromophenol blue, was within 1 cm of the bottom. Individual polypeptide bands were visualized by Coomassie Blue staining and the molecular weight of the individual polypeptides determined by their migration in relation to the migration of protein standards of known molecular weight. The molecular weight standards ranged from 200,000 daltons to 14,400 daltons. This technique revealed 31 polypeptides with the following relative molecular weights; 300, 215, 145, 115, 100, 94, 84, 74, 68, 59, 51, 50, 48, 45, 44, 41.5, 40, 36, 34, 31, 29, 27, 26, 25, 24, 22, 21.5, 19, 17, 15.5 and 13 kd.

EXAMPLE 4

Production of Anti-Sporozoite Antibodies

E. acervulina sporozoite immunogen was prepared as detailed in Example 2. Antisera was prepared in NZW rabbits by subcutaneous (SC) immunization at multiple sites with a total of 100 μg protein equivalent of sporozoite immunogen emulsified in Complete Freund's Adjuvant. Rabbits were boosted SC with 100 μg protein equivalent of sporozoite immunogen in Incomplete Freund's (IFA) at days 36, 48 and 84 after the primary immunization, bled 10 days after the last injection and sera prepared.

EXAMPLE 5

Characterization of E. acervulina Sporozoite Surface Antigen Immune Sera

DE-52-purified E. acervulina sporozoites were prepared as detailed in Example 2. Rabbit anti-E. acervulina sporozoite immune sera were prepared as detailed in Example 4.

The ability of this antisera to agglutinate E. acervulina sporozoites was determined using 96-well assay plates. A sporozoite suspension, 0.05 ml, containing $4 \times 10^6$ sporozoites per ml was added to each well with 0.05 ml of diluted serum. Normal preimmune rabbit sera and rabbit anti-E. acervulina sporozoite immune sera were assayed at double dilutions from 1/100 to 1/12,800.

The mixtures were incubated at 41° C. for 1 hour and examined microscopically for agglutination and/or lysis (due to the presence of complement in the sera). Normal rabbit serum had no detectable effects on the sporozoites; neither agglutination nor lysis was observed. The rabbit immune serum lysed parasites at dilutions of 1/200 and agglutinated sporozoites at dilutions of 1/3200.

Rabbit sera were also tested for their ability to neutralize E. acervulina sporozoite infectivity in vivo. E. acervulina sporozoites were incubated with either normal rabbit serum or rabbit anti-E. acervulina sporozoite immune serum at dilutions of 1/100 for 1 hour at 41° C. Either 30,000 or 100,000 treated sporozoites were then injected into the upper intestine of groups of 5 chickens. Five days after inoculation the intestines were removed and examined for lesions which were scored according to Johnson and Reid, Exp. Parasit. 28: 30–36, (1970). The following results were obtained.

|  | Number of Sporozoites Injected | |
|---|---|---|
|  | 30,000 | 100,000 |
| Serum | Mean Group Lesion Score | Mean Group Lesion Score |
| Normal Rabbit | 2.0 | 2.8 |
| Rabbit Anti-E. Acervulina | 1.2 | 2.0 |

These results show, that rabbit anti-Eimeria antibodies bind to the surface of intact sporozoites and neutralize the infectivity of the transferred sporozoites. This data further demonstrates that sporozoite immunogens induce antibodies which will inhibit the production of coccidiosis.

EXAMPLE 6

Characterization of the Immunodominant Polypeptide Antigens in the Protective Extract of E. acervulina Sporozoites Fifty μg of sporozoite immunogen was separated into component polypeptides as detailed in Example 3, by sodium dodecyl sulfate polyacrylamide gel electrophoresis. After separation they were transferred to nitrocellulose paper following the procedures of Erickson et al., J. Imm. Meths. 51: 241–249 (1982) and Towbin et al., P.N.A.S. 76: 4350 (1979). A Biorad Transblot apparatus was used for this transfer with a voltage gradient of 3.5 V/cm being applied for 21 hours at 11° C.

Immunodominant polypeptides in the transferred sporozoite immunogen were located using rabbit antisera prepared as detailed in Example 4. This serum was diluted to 1:100 with 0.25% gelatin-TEN (0.05M tris, 0.14M NaCl, 0.005M EDTA, 0.05% Triton X100). After washing, goat anti-rabbit IgG conjugated to horseradish peroxidase was added to the nitrocellulose paper containing the transferred polypeptides. The peroxidase substrate 4 chloro-1-naphthol was applied to the nitrocellulose paper and formed a visible reaction product at the site of the polypeptide-antibody complex. Twenty polypeptides in the sporozoite extract reacted with this antisporozoite sera. These are molecules of 115, 84, 74, 68, 65, 59, 45, 41.5, 37, 34, 31, 29 27, 26.5, 26, 24, 23, 22.5, 21.5 and 20 kd relative molecular weight.

EXAMPLE 7

Intramuscular Immunization of Three-Week-Old Chickens Against Coccidiosis with an Extract of E. acervulina Sporulated Oocysts (PGS)

Female broiler chickens (Hubbard Farms) were immunized intramuscularly with different doses of PGS composite immunogen as detailed in Example 1. The dosage was based on protein content as determined by the method of Lowry et al., supra, and was given once weekly on four occasions, starting at three weeks of age. The experimental and control chickens were challenged one week after the last immunization with an oral inoculation of $3 \times 10^5$ virulent E. acervulina sporulated oocysts. Six days after challenge the chickens were killed and the severity of the lesions in the intestine were determined according to the method of Johnson and Reid, supra. The lesions were scored on a defined scale of 1 to 4 where 4 is the most severe. Fecal oocyst counts were determined by hemocytometer counts of material derived by salt flotation according to a standard technique. The following results were obtained.

| Group | Dose (μg) | Number of Birds | Mean Group Lesion Score | Mean Group Oocyst Count |
|---|---|---|---|---|
| 1 | 10 | 5 | 1.2 | $6.0 \times 10^5$ |
| 2 | 25 | 5 | 1.0 | $8.0 \times 10^5$ |
| 3 | 50 | 5 | 1.6 | $2.7 \times 10^6$ |
| 4 | 100 | 5 | 1.4 | $3.2 \times 10^6$ |
| 5 | 200 | 5 | 3.2 | $1.0 \times 10^7$ |
| 6 | None | 5 | 3.5 | $1.3 \times 10^7$ |

These results show that PGS composite immunogen, an extract from E. acervulina sporulated oocysts which contains no viable or intact parasites, can be used to immunize 3-week-old broiler chickens. An intrasmuscular inoculation provides a high level of protection against the disease as indicated by the absence of severe lesion development in immune birds after a normally virulent infection. Immunity is also manifest by a reduction in oocyst counts in vaccinated birds.

EXAMPLE 8

Intrasmuscular Immunization of Two-Day-Old Chickens Against Coccidiosis with an Extract of *E. acervulina* Sporulated Oocysts (PGS)

Female broiler chicks (Hubbard Farms) were immunized with different doses of PGS composite immunogen as detailed in Example 1. The dosage was based on protein content as determined by the method of Lowry et al., supra, and was given intramuscularly on days 2, 9 and 16 following hatching. Experimental and control chickens were challenged one week after the last immunization with an oral inoculation of $5 \times 10^5$ *E. acervulina* sporulated oocysts. Six days after challenge the chickens were killed and the severity of the lesions in the intestine were determined according to the method of Johnson and Reid, supra. The lesions were scored as detailed in Example 7. The following results were obtained.

| Group | Dose (μg) | Number of Birds | Mean Group Lesion Score |
| --- | --- | --- | --- |
| 1 | 1 | 8 | 2.6 |
| 2 | 10 | 8 | 1.3 |
| 3 | 50 | 8 | 1.8 |
| 4 | None | 5 | 3.4 |

These results show that PGS, an extract from *E. acervulina* sporulated oocysts, which contains no viable or intact parasites, can be used to immunize chickens when given at a very early age. The PGS composite immunogen provides a high level of protection against the disease as indicated by the absence of severe lesions developing in immune birds after a normally virulent infection.

EXAMPLE 9

Oral Immunization of Two and One-Half-Week-Old Chickens Againt Coccidiosis with an Extract of *E. acervulina* Sporulated Oocysts (PGS)

Female broiler chicks (Hubbard Farms) were immunized with different doses of PGS composite immunogen as detailed in Example 1. The dosage was based on protein content as determined by the method of Lowry et al., supra, and was given by the oral route at weekly intervals on 4 occasions. Experimental and control chickens were challenged 8 days after the last immunization with an oral inoculation of $3 \times 10^5$ *E. acervulina* infective sporulated oocysts. Six days after challenge the chickens were killed and the severity of the lesions in the intestine were determined according to the method of Johnson and Reid, supra. The lesions were scored as detailed in Example 7. The following results were obtained.

| Group | Dose (μg) | Number of Birds | Mean Group Lesion Score |
| --- | --- | --- | --- |
| 1 | 10 | 5 | 1.4 |
| 2 | 25 | 5 | 1.4 |
| 3 | 50 | 5 | 0.8 |
| 4 | 100 | 5 | 2.0 |
| 5 | 200 | 5 | 2.4 |
| 6 | None | 5 | 3.0 |

These results show that chickens can be immunized with PGS, an extract from *E. acervulina* sporulated oocysts, which contains no viable or intact parasites, by the oral route of inoculation. The resultant immunity offers a high level of protection against the disease as indicated by the absence of severe lesions following a normally virulent infection.

EXAMPLE 10

Intramuscular Immunization of Two-Day Old Chickens Against Coccidiosis with an Extract of *E. acervulina* Sporozoites Female broiler chicks (Hubbard Farms) were immunized with different doses of sporozoite immunogen as detailed in Example 3. The dosage was based on protein content as determined by the method of Lowry et al., supra, and was administered intramuscularly on days 2, 9 and 16 following hatching. Experimental and control chickens were challenged six days after the last immunization with an oral inoculation of $5 \times 10^5$ infective *E. acervulina* sporulated oocysts. Six days after challenge the chickens were killed and the severity of the lesions in the intestine were determined according to the method of Johnson and Reid, supra. The lesions were scored as detailed in Example 7. The following results were obtained.

| Group | Dose (μg) | Number of Birds | Mean Group Lesion Score |
| --- | --- | --- | --- |
| 1 | 0.01 | 8 | 3.3 |
| 2 | 0.1 | 8 | 3.0 |
| 3 | 1.0 | 8 | 2.0 |
| 4 | 10.0 | 8 | 1.9 |
| 5 | None | 8 | 3.3 |

These results show that sporozoite immunogens extracted from *E. acervulina* can be used to immunize very young chickens against infection with *E. acervulina* sporulated oocysts. The chickens showed a high level of immunity as indicated by the general absence of severe lesions following challenge with an infective dose.

EXAMPLE 11

Intramuscular Immunization of Two-Day-Old Chickens Against Coccidiosis Caused by *E. acervulina, E. tenella* and *E. maxima* with an Extract of *E. acervulina* Sporulated Oocysts (PGS)

Female broiler chicks (Hubbard Farms) were immunized with different doses of PGS composite immunogen as detailed in Example 1. The dosage was based on protein content as determined by the method of Lowry et al., supra, and was given by the intramuscular route on days 2, 9 and 16 following hatching. Experimental and control chickens were challenged one week after the last immunization with an oral inoculation of eithr $5 \times 10^5$ *E. acervulina*, $5 \times 10^4$ *E. tenella* or $2 \times 10^5$ *E. maxima* sporulated oocysts. Six days later the chickens were killed and the severity of the lesions in the ceca or intestine were determined according to the method of Johnson and Reid, supra. The lesions were scored as detailed in Example 7. The following results were obtained.

| Challenge Species | MEAN GROUP LESION SCORES[1] PGS Dose (μg) | | | | |
|---|---|---|---|---|---|
| | 0.1 | 1.0 | 10.0 | 50.0 | None |
| E. acervulina | 1.9 | 3.0 | 1.7 | 2.2 | 3.4 |
| E. tenella | 1.6 | 2.8 | 1.9 | 2.6 | 3.5 |
| E. maxima | 3.2 | 1.9 | 1.8 | 3.3 | 3.7 |

[1]There were 7 chickens in each group.

These results are the first to conclusively show that immunity to the immunogens of one species of Eimeria also protect against infection with other Eimeria species. Indeed, the level of protection against the non-immunizing species was equivalent to that of the species used to vaccinate the chickens.

EXAMPLE 12

Intramuscular Immunization of Two-Day-Old Chickens Against Coccidiosis Caused by E. acervulina, E. tenella and E. maxima with an Extract of E. acervulina Sporozoites Female broiler chicks (Hubbard Farms) were immunized with different doses of sporozoite immunogen as detailed in Example 2. The dosage was based on protein content as determined by the method of Lowry et al., supra, and was given by the intramuscular route on days 2, 9 and 16 following hatching. Experimental and control chickens were challenged one week after the last immunization with an oral inoculation of either $5 \times 10^5$ E. acervulina, $5 \times 10^3$ E. tenella, or $2 \times 10^5$ E. maxima sporulated oocysts. Six days later the chickens were killed and the severity of the lesions in the ceca or intestine were determined according to the method of Johnson and Reid, supra. The lesions were scored as detailed in Example 7. The following results were obtained.

| Challenge Species | MEAN GROUP LESION SCORES[1] Sporozoite Antigen Dose (μg) | | | | |
|---|---|---|---|---|---|
| | 0.01 | 0.1 | 1.0 | 10.0 | None |
| E. acervulina | 3.3 | 3.0 | 2.0 | 1.9 | 3.3 |
| E. tenella | 3.0 | 3.1 | 2.6 | 2.0 | 3.2 |
| E. maxima | 3.4 | 3.3 | 2.8 | 2.1 | 3.3 |

[1]There were 7 chickens in each group.

These results show that sporozoite immunogens, an extract from purified E. acervulina sporozoites which contains no viable or intact parasites, can be used to immunize chickens against infectious oocysts of E. acervulina, E. tenella and E. maxima. The level of immunity against the non-immunizing species was equivalent to that of the species used to vaccinate the chickens.

What is claimed is:

1. An immunogenic composite obtained from Eimeria acervulina sporulated oocysts by grinding, collecting the supernatant fluid by centrifugation, freezing and thawing the supernatant fluid and sonicating the supernatant fluid which is capable of immunizing against coccidiosis.

2. A method of immunizing chickens against coccidiosis comprising administering an effective immunizing amount of the immunogenic composite of claim 1.

3. An immunizing composition for confering on chickens active immunity against coccidiosis which comprises an effective immunizing amount of the immunogenic composite of claim 1 in a physiologically acceptable medium.

4. A sporozoite immunogen obtained by disrupting a suspension of Eimeria acervulina sporozoites, the disrupted material containing polypeptides capable of immunizing against coccidiosis.

5. The sporozoite immunogen of claim 4 having immunogenic polypeptides having molecular weights of 115, 84, 74, 68, 65, 59, 45, 41.5, 37, 34, 31, 29, 27, 26.5, 26, 24, 23, 22.5, 21.5 and 20 kd against which polyclonal antibodies specific to Eimeria acervulina react.

6. A method of immunizing chickens against coccidiosis comprising administrating an effective immunizing amount of the sporozoite immunogen of claim 4.

7. A sporozoite immunogen composition capable of protecting against coccidiosis comprising an effective amount of the sporozoite immunogen of claim 5 in a physiologically acceptable medium.

8. A composition according to claim 7 wherein the sporozoite immunogen is present in an amount of from about 1 μg to about 200 μg.

9. A composition according to claim 8 wherein the sporozoite immunogen is present in an amount of from about 5 μg to about 75 μg.

* * * * *

UNITED STATES PATENT AND TRADEMARK OFFICE
CERTIFICATE OF CORRECTION

PATENT NO. : 4,724,145

DATED : 2/9/88

INVENTOR(S) : Peter K. Murray, Balbir S. Bhogal, Ethel B. Jacobson, Mark S. Crane, Dennis M. Schmatz, and Stefan Galuska It is certified that error appears in the above-identified patent and that said Letters Patent is hereby corrected as shown below:

On the Title page under heading [75],
1. after Peter K. Murray, delete "Red Bank" and replace with --Hambldon Surry, U.K.--
2. after Balbir S. Bohgal, delete "Avenel, both of NJ" and replace with --Midlothian, VA--
3. after "North Plainfield, NJ" add --Thomas T. MacDonald, Herts, U.K.--.

Signed and Sealed this

Fifth Day of September, 1989

Attest:

DONALD J. QUIGG

Attesting Officer

Commissioner of Patents and Trademarks